United States Patent [19]

Siegel et al.

[11] Patent Number: 5,801,272
[45] Date of Patent: Sep. 1, 1998

[54] PREPARATION OF MIXTURES OF (R)- AND (S)-2-(4-ALKANOYLPHENOXY)- OR (R)- AND (S)-2-(4-AROYLPHENOXY)PROPIONIC ESTERS

[75] Inventors: Wolfgang Siegel; Hubert Sauter, both of Mannheim; Gerhard Schaefer, Heidelberg, all of Germany

[73] Assignee: BASF Aktiengesellschaft, Ludwigshafen, Germany

[21] Appl. No.: 522,291

[22] PCT Filed: May 26, 1994

[86] PCT No.: PCT/EP94/01684

§ 371 Date: Aug. 11, 1995

§ 102(e) Date: Aug. 11, 1995

[87] PCT Pub. No.: WO94/27950

PCT Pub. Date: Dec. 8, 1994

[30] Foreign Application Priority Data

Jun. 1, 1993 [DE] Germany ............ 43 18 092.2

[51] Int. Cl.⁶ ............................................. C07C 69/76
[52] U.S. Cl. ..................................... 560/52; 560/51
[58] Field of Search ........................................ 560/52

[56] References Cited

U.S. PATENT DOCUMENTS

| | | | |
|---|---|---|---|
| 3,383,411 | 5/1968 | Schultz et al. | 560/52 |
| 3,954,442 | 5/1976 | Becker et al. | |
| 4,173,709 | 11/1979 | Metivier et al. | |
| 4,332,960 | 6/1982 | Troesken et al. | |
| 4,447,256 | 5/1984 | Ohyama et al. | |
| 4,528,394 | 7/1985 | Otterbacher. | |
| 4,629,493 | 12/1986 | Ura et al. | |
| 4,753,673 | 6/1988 | Johnston et al. | |
| 4,978,774 | 12/1990 | Schlegel et al. | |
| 5,068,052 | 11/1991 | Watanabe et al. | |

FOREIGN PATENT DOCUMENTS

| | | |
|---|---|---|
| 129 034 | 12/1984 | European Pat. Off. |
| 248 968 | 12/1987 | European Pat. Off. |
| 323 127 | 7/1989 | European Pat. Off. |
| 380 043 | 8/1989 | European Pat. Off. |
| 334 595 | 9/1989 | European Pat. Off. |
| 334 596 | 9/1989 | European Pat. Off. |
| 334 597 | 9/1989 | European Pat. Off. |
| 334 598 | 9/1989 | European Pat. Off. |
| 1 543 841 | 1/1970 | Germany. |
| 1 768 582 | 10/1971 | Germany. |
| 2 204 973 | 8/1973 | Germany. |
| 22 23 894 | 12/1973 | Germany. |
| 1 410 542 | 10/1975 | Germany. |
| 24 33 067 | 1/1976 | Germany. |
| 30 04 770 | 8/1980 | Germany. |
| 32 46 847 | 6/1983 | Germany. |
| 1102271 | 2/1968 | United Kingdom. |
| 2 091 248 | 7/1982 | United Kingdom. |

OTHER PUBLICATIONS

Chem Abst. J6 2178–543.

*Primary Examiner*—Paul J. Killos
*Attorney, Agent, or Firm*—Keil & Weinkauf

[57] ABSTRACT

A mixture of (R)- and (S)-2-(4-alkanoylphenoxy)- or (R)- and (S)-2-(4-aroylphenoxy)propionic esters I

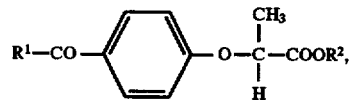

with an enantiomeric excess of at least 90% is prepared by reacting a mixture of (R) and (S) enantiomer of a 2-phenoxypropionic ester II

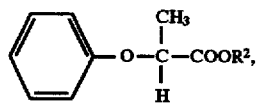

in which the appropriate (R) or (S) isomer is present in excess, with a carboxylic acid derivative of the formula III

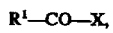

(X=OH, halogen, R¹COO or sulfonyloxy)
in the presence of a Friedel-Crafts catalyst.

The (R)- or (S)-2-(4-alkanoylphenoxy)propionic esters and (R)- or (S)-2-(4-hydroxyphenoxy)propionic esters are used for preparing crop protection agents and drugs.

4 Claims, No Drawings

PREPARATION OF MIXTURES OF (R)- AND (S)-2-(4-ALKANOYLPHENOXY)- OR (R)- AND (S)-2-(4-AROYLPHENOXY)PROPIONIC ESTERS

DESCRIPTION

The present invention relates to a novel process for preparing a mixture of (R)- and (S)-2-(4-alkanoylphenoxy)- or (R)- and (S)-2-(4-aroylphenoxy)propionic esters of the general formula I

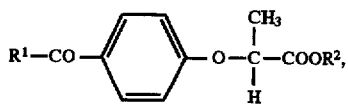

where $R^1$ is aryl, alkyl or aralkyl, and $R^2$ is alkyl, where the mixture contains an enantiomeric excess of at least 90 mol % of (R) or (S) isomer.

The present invention also relates to the preparation of a mixture of (R)- and (S)-2-(4-acyloxyphenoxy)propionic esters of the formula IV

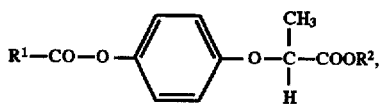

which contains an enantiomeric excess of at least 90 mol % of (R) or (S) isomer,
by oxidizing a mixture of (R)- and (S)-2-(4-alkanoylphenoxy)- or (R)- and (S)-2-(4-aroylphenoxy) propionic esters I, which contains the appropriate (R) or (S) isomer in said excess, with performic acid or with a mixture of hydrogen peroxide and formic acid.

The present invention furthermore relates to the preparation of a mixture of (R)- and (S)-2-(4-hydroxyphenoxy)propionic acid and/or an alkyl ester of this acid by oxidizing a mixture of the (R) and (S) enantiomers of a 2-(4-alkanoylphenoxy)- or 2-(4-aroylphenoxy)propionic ester I, which contains the appropriate (R) or (S) isomer in excess, and hydrolyzing the resulting mixture of (R)- and (S)-2-(4-acyloxyphenoxy)propionic esters IV with water or aliphatic alcohols in the presence of acidic catalysts.

2-(4-Hydroxyphenoxy)propionic acid and its alkyl esters are valuable intermediates for synthesizing crop protection agents and drugs. They are particularly suitable for preparing herbicidal 2-(4-aryloxyphenoxy)- and 2-(4-hetaryloxyphenoxy)propionic acid derivatives (cf., for example, BE-A 868 875, BE-A 858 618, DE-A 22 23 894, DE-A 24 33 067, DE-A 25 76 251, DE-A 30 04 770, DE-A 32 46 847, EP-A 54 715, EP-A 248 968, EP-A 323 127 and U.S. Pat. No. 4,753,673) in which the herbicidal activity normally derives from one enantiomer. It is therefore desirable also to prepare with maximum enantiomeric purity the intermediates I and IV as well as 2-(4-hydroxyphenoxy) propionic acid and its alkyl esters required to prepare the active substances.

The 2-(4-alkanoylphenoxy)- and 2-(4-aroylphenoxy) propionic esters I are normally prepared by Williamson's ether synthesis from 4-hydroxyphenyl alkyl ketones or 4-hydroxyphenyl aryl ketones and 2-halo- or 2-sulfonyloxypropionic acid derivatives under basic conditions (cf. Acta Polon. Pharm. 20 (1963) 25–30 (see also CA 61 (1964) 8225e), JP 62 178 543, EP-A 0 129 034, EP-A 0 334 595, EP-A 0 334 596, EP-A 0 334 597 and EP-A 0 334 598). However, pure enantiomers cannot be obtained by this method because, according to EP-A 0 380 043, the preferred reaction temperatures for the ether synthesis (80°–100° C.) bring about racemization. The unwanted enantiomer must accordingly first be removed in a subsequent purification step, which is industrially elaborate.

In order to make the optically active 2-(4-acetylphenoxy) propionic esters more accessible, EP-A 0 380 043 proposes carrying out the reaction at temperatures below 50° C. Nevertheless, racemization cannot be completely avoided in every case.

It is furthermore generally known (cf., for example, G. A. Olah, Friedel-Crafts and Related Reactions vol. 3, pages 48 to 50 and 180 to 188, John Wiley & Sons, Inc. (1964) and D. E. Pearson, C. A. Buehler, Synthesis (1972) 533) to react achiral aryl alkyl ethers of the formula V with carboxylic acid derivatives in a Friedel-Crafts acylation:

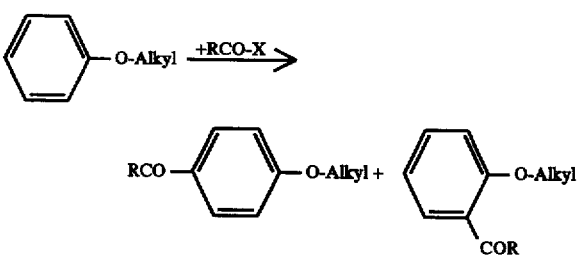

However, in this case it is unsatisfactory that the 4-acylaryl alkyl ethers are accompanied as by-products by 2-acylaryl alkyl ethers. Thus, for example, the benzoylation of anisole with benzoyl chloride/iron(III) chloride at 150° C. yields 90% para- and 10% ortho-acylation product (cf. DE-A 22 04 973). Separation of the two isomers, eg. by chromatography or distillation, is usually elaborate and associated with loss of required product.

According to EP-A 0 129 034, EP-A 0 334 595, EP-A 0 334 596, EP-A 0 334 597 and U.S. Pat. No. 4,528,394, the 2-(4-acylphenoxy)propionic esters can be converted by oxidation with peracids or peroxide and subsequent hydrolysis into 2-(4-hydroxyphenoxy)propionic esters.

It was an object of the present invention to make the optically active compounds I more accessible in a simple and economic manner.

Accordingly this object was achieved by a process for preparing mixtures of (R)- and (S)-2-(4-alkanoylphenoxy)- or (R)- and (S)-2-(4-aroylphenoxy)propionic esters, which comprises reacting a mixture of (R) and (S) enantiomer of a 2-phenoxypropionic ester of the formula II

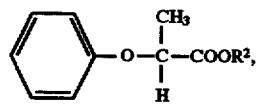

in which the appropriate (R) or (S) isomer is present in said excess, with a carboxylic acid derivative of the formula III

$R^1$—CO—X,          III where X is hydroxyl, halogen, $R^1COO$ or a sulfonyloxy radical, in the presence of a Friedel-Crafts catalyst.

We have also found a process for preparing a mixture of (R)- and (S)-2-(4-acyloxyphenoxy)propionic esters of the formula IV and a process for preparing a mixture of (R)- and (S)-2-(4-hydroxyphenoxy)propionic acid and/or an alkyl ester of this acid.

The optically active 2-phenoxypropionic esters II are known, eg. from DE-A 15 43 841, or can be prepared in the manner described therein.

The carboxylic acid derivatives III are likewise generally known. For the preparation of starting compounds III with X=sulfonyloxy, for example alkanesulfonyloxy such as methanesulfonyloxy, haloalkanesulfonyloxy such as trifluoromethanesulfonyloxy or arylsulfonyloxy such as p-toluenesulfonyloxy, reference may be made, for example, to J. Org. Chem. 36 (1971) 528–531 and Chem. Ber. 116 (1983) 1183–1194.

The process according to the invention is normally carried out in an inert solvent or diluent, suitable examples being chlorinated hydrocarbons such as dichloromethane, chloroform, 1,2-dichloroethane, chlorobenzene and dichlorobenzenes, aliphatic hydrocarbons such as hexane, heptane and octane, aliphatic carboxylic esters such as methyl, ethyl, propyl, n-butyl and isobutyl acetates, as well as nitrobenzene or carbon disulfide. The chlorinated hydrocarbons are particularly preferred, especially dichloromethane, chloroform, 1,2-dichloroethane and 1,2-dichlorobenzene.

Friedel-Crafts catalysts mean, in particular, Lewis acids such as aluminum trichloride, iron(III) chloride, boron trifluoride, titanium tetrachloride, tin tetrachloride and zinc chloride or Brönsted acids such as hydrofluoric acid, sulfuric acid, phosphoric acid, phosphoric acid/$BF_3$ complexes, methanesulfonic acid and trifluoromethanesulfonic acid.

The Friedel-Crafts catalyst is normally used in stoichiometric, less than stoichiometric or catalytic amounts based on the carboxylic acid derivative III. However, it is also possible to employ an excess of Friedel-Crafts catalyst. Good yields of I are normally obtained with 0.05–10, preferably 0.05–2.5, mole equivalents of Friedel-Crafts catalyst per mole of carboxylic acid derivative III.

For complete reaction, at least equimolar amounts of 2-phenoxypropionic ester II and carboxylic acid derivative III are necessary. However, it is advantageous to use a 0.1–10-fold molar excess of carboxylic acid derivative III based on the amount of II.

In general, the reaction takes place sufficiently quickly at from −30° to +180° C. When aliphatic carboxylic acid derivatives III are used, temperatures from −20° to 70° C. have proven particularly advantageous. Higher temperatures, from 25° to 180° C., are particularly advisable when aromatic carboxylic acid derivatives III are used.

The reaction can be carried out under atmospheric or superatmospheric pressure. It is expediently carried out under atmospheric pressure or the autogenous pressure of the particular diluent.

The progress of the reaction can be followed by conventional analytical methods such as thin-layer chromatography, high-pressure liquid chromatography and gas chromatography.

The product I is expediently isolated by conventional processes such as distillation, filtration, centrifugation or by adding water and subsequently extracting.

The reaction can be carried out either batchwise, eg. in a stirred reactor, or continuously, for example in a reaction tube or a cascade of stirred reactors.

The resulting crude products can, if required, be further purified, eg. by crystallization, rectification or chromatographic methods.

The Friedel-Crafts acylation according to the invention of the mixture of (R)- and (S)-2-phenoxypropionic esters II with carboxylic acid derivatives III leads to good yields of mixtures of (R)- and (S)-2-(4-alkanoylphenoxy)- or 2-(4-aroylphenoxy)propionic esters I with a para selectivity of more than 99%. This means the removal of an unwanted ortho isomer is unnecessary. Furthermore, it is particularly advantageous that the enantiomeric excess is completely retained in the reaction. The reaction of a mixture of (R)- and (S)-2-phenoxypropionic ester II with an excess of (R) or (S) enantiomer of more than 90%, preferably more than 94%, accordingly leads to mixtures of enantiomers I with at least the same enantiomeric excess. The products I can, either without further purification or, preferably, after isolation, be oxidized by the Baeyer-Villiger method described in J. Amer. Chem. Soc. 71 (1949) 14, J. Amer. Chem. Soc. 72 (1950) 5515, J. Amer. Chem. Soc. 80 (1958) 6393, JP 62 178 543, EP-A 0 334 595, EP-A 0 334 596 and EP-A 0 334 597 for compounds of this type to give the corresponding mixtures of (R)- and (S)-2-(4-acyloxyphenoxy)propionic esters IV

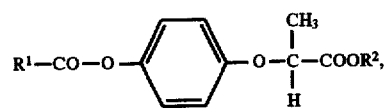

with, once again, complete retention of the stereochemical purity (above 90 mol %, in particular above 94 mol %, enantiomeric excess).

The oxidation is normally carried out in an inert solvent, eg. in a chlorinated hydrocarbon such as dichloromethane and chloroform, an aromatic hydrocarbon such as chlorobenzene, the dichlorobenzenes, toluene and o-, m- or p-xylene, an aliphatic carboxylic ester such as ethyl acetate, an aliphatic carboxylic acid such as acetic acid, an aliphatic alcohol such as methanol, ethanol, n-propanol and isopropanol, or in water.

Examples of suitable oxidizing agents are hydrogen peroxide and organic peracids such as performic acid, peracetic acid, trifluoroperacetic acid, m-chloroperbenzoic acid and perphthalic acid, especially performic acid and mixtures of hydrogen peroxide and formic acid. Mixtures of hydrogen peroxide and formic acid are particularly preferred.

Normally 1–3 equivalents of the oxidizing agent based on the amount of I are sufficient for complete oxidation.

The oxidation can be carried out under atmospheric pressure or under reduced pressure, and the reaction temperature is normally from 0° to 100° C.

The mixtures of optically active 2-(4-acyloxyphenoxy) propionic esters IV can in turn be converted with water or aliphatic alcohols (with up to about 20 carbon atoms) in the presence of acids such as hydrochloric acid, sulfuric acid, toluenesulfonic acid, methanesulfonic acid into mixtures of (R)- and (S)-2-(4-hydroxyphenoxy)propionic acid (cf. Houben-Weyl, Methoden der Organischen Chemie, vol. E5, Georg Thieme Verlag, Stuttgart 1985, pp. 225–226) and/or an alkyl ester of this acid (Houben-Weyl, ditto, vol. E5, p. 702). In this reaction too there is retention of the enantiomeric excess of (R) or (S) enantiomer in the initial mixture, ie. above 90 mol %, in particular above 94 mol %.

The process according to the invention can be generally applied to the synthesis of mixtures of (R)- and (S)-2-(4-alkanoylphenoxy)- or (R)- and (S)-2-(4-aroylphenoxy)-($C_1$-$C_6$-alkyl)carboxylic esters.

Among the defined mixtures of optically active compounds I and IV, those which are particularly preferred are the ones in which the radicals $R^1$ and $R^2$ have the following meanings:

$R^1$—unsubstituted or substituted aryl, in particular phenyl or naphthyl, both of which may also have from one to three of the following substituents: halogen, nitro and/or $C_1$-$C_4$-alkyl;

$C_1$–$C_{20}$-alkyl, in particular $C_1$–$C_6$-alkyl, which can be unsubstituted or carry an unsubstituted or substituted aryl radical as specified above;

$R^2$ hydrogen, $C_1$–$C_{20}$-alkyl, especially $C_1$–$C_6$-alkyl.

With a view to the preferred use of the products I, IV, 2-(4-hydroxyphenoxy)propionic acid and the alkyl 2-(4-hydroxyphenoxy)propionates for the preparation of active substances in crop protection, the mixtures which are particularly preferably prepared are ones in which the (R) enantiomer is present in an excess of at least 90, particularly preferably at least 94, mol %.

PREPARATION EXAMPLES

Example 1

Methyl (R)-2-(4-acetylphenoxy)propionate

Precursor: methyl (R)-2-phenoxypropionate

A mixture of 500 g (3.0 mol) of (R)-2-phenoxypropionic acid (94–95% enantiomeric excess), 1500 ml of methanol and 10 ml of methanol saturated with hydrogen chloride was refluxed for 3 hours. The mixture was then concentrated under reduced pressure, and the crude product was distilled at 95°–97° C. under 0.1 mbar. Yield: 94.9% (94–95% enantiomeric excess).

Methyl (R)-2-(4-acetylphenoxy)propionate (according to the invention):

90.1 g (1.125 mol) of acetyl chloride were added dropwise to a mixture of 150 g (1.125 mol) of aluminum trichloride in 750 ml of dichloromethane at 5° C. over the course of 30 minutes. The resulting mixture was stirred at 5° C. for 30 minutes and then, at this temperature, a solution of 81.1 g (0.45 mol) of methyl (R)-2-phenoxypropionate in 90 ml of dichloromethane was added dropwise over the course of 60 minutes. The mixture was then stirred at 5° C. for 60 minutes and subsequently hydrolyzed with 2 kg of ice. The organic phase was then separated off, dried over sodium sulfate and concentrated under reduced pressure. The crude product was purified by vacuum distillation at 135°–140° C. under 0.1 mbar. Yield: 96% (94–95% enantiomeric excess). Content of methyl (R)-2-(2-acetylphenoxy)propionate: below 0.2%.

Example 2 (Comparative Example)

Example 1 was repeated with 48.66 g (0.45 mol) of anisole in place of methyl (R)-2-phenoxypropionate. The product comprised 98.7% 4-methoxyacetophenone and 1.3% 2-methoxyacetophenone.

Examples 3 to 13 (According to the Invention)

The acid chlorides listed in the following Table 1 were reacted with methyl or isobutyl (R)-2-phenoxypropionate as in Example 1:

TABLE 1

| Ex. No. | Acid chloride (III); $R^1$ = | Phenoxypropionic ester (II) | Molar ratio II:III:AlCl$_3$ | Solvent | Temp. [°C] | Yield of I*) |
|---|---|---|---|---|---|---|
| 3 | Methyl | Methyl ester | 1:1:1 | Dichloromethane | 20 | 31.9 |
| 4 | Methyl | Methyl ester | 1:2.1:2.1 | Dichloromethane | 20 | 97.6 |
| 5 | Methyl | Methyl ester | 1:2.5:2.5 | Dichloromethane | 20 | 98.1 |
| 6 | Methyl | Methyl ester | 1:1:2.5 | Dichloromethane | 5 | 98.7 |
| 7 | Methyl | Methyl ester | 1:1:2.1 | Dichloromethane | 20 | 97.1 |
| 8 | Methyl | Methyl ester | 1:1:2.1 | Chlorobenzene | 5 | 87.1 |
| 9 | Methyl | Methyl ester | 1:1:2.1 | 1,2-Dichloro-benzene | 5 | 91.3 |
| 10 | Ethyl | Methyl ester | 1:2.5:2.5 | Dichloromethane | 5 | 96.2 |
| 11 | 1-Chloromethyl | Methyl ester | 1:2.5:2.5 | Dichloromethane | 5 | 79.4 |
| 12 | (S)-1-Chloroethyl | Methyl ester | 1:2.5:2.5 | Dichloromethane | 20 | 92.9 |
| 13 | Methyl | iso-Butyl ester | 1:2.5:2.5 | Dichloromethane | 5 | 95.6 |

*)in percent; enantiomeric excess according to HPLC analysis = 94–95%
The stirring time was 3 hours, but 5 hours in Examples 3, 6 and 11.

Example 14 (According to the Invention)

Methyl (R)-2-(4-acetylphenoxy)propionate

A mixture of 36 g (0.2 mol) of methyl (R)-2-phenoxypropionate (enantiomeric excess 94–95%), 81.6 g (0.8 mol) of acetic anhydride, 6.5 g (0.04 mol) of iron(III) chloride and 100 ml of ethyl acetate was heated at 70°–75° C. for 6 hours. The diluent and excess acetic anhydride were then removed under reduced pressure, after which the crude product was subjected to vacuum distillation. Yield: 80% (94–95% enantiomeric excess).

Example 15 (According to the Invention)

Methyl (R)-2-(4-acetylphenoxy)propionate 67 g (1 mol) of boron trifluoride were passed into 60 g (1 mol) of acetic acid. The mixture was heated to 45°–50° C., and 36 g (0.2 mol) of methyl (R)-2-phenoxypropionate were added. After stirring at 45°–50° C. for 7 hours, the temperature was raised to 80° C. for 1 h and the mixture was then stirred into 800 ml of 25% by weight aqueous sodium acetate solution. The product was extracted with 200 ml of ethyl acetate and, after concentration of the organic phase, purified by vacuum distillation. Yield: 83.7% (94–95% enantiomeric excess).

Examples 16 to 18 (According to the Invention)

Methyl (R)-2-(4-aroylphenoxy)propionate 10 g (55 mmol) of methyl (R)-2-phenoxypropionate (enantiomeric excess 94–95%), 60 mmol of the aroyl chlorides indicated in the following Table 2 and 320 mg (2 mmol) of iron(III) chloride were heated with stirring at the temperature likewise stated in Table 2. After 3 hours, the methyl (R)-2-(4-aroylphenoxy)propionates were purified by distillation at 200°–250° C. under 0.1 mbar (in a Kugelrohr heater).

TABLE 2

| Example | Aroyl chloride | Temperature | Yield of product |
|---|---|---|---|
| No. 16 | Benzyl chloride | 170° C. | 86.9% |
| No. 17 | p-Chlorobenzoyl chloride | 150° C. | 88.4% |
| No. 18 | p-Nitrobenzoyl chloride | 180° C. | 86.4% |

Example 19

Methyl (R)-2-(4-acetoxyphenoxy)propionate 54.4 g (0.48 mol) of a 30% strength solution of hydrogen peroxide in water was added dropwise to the solution of 88.93 g (0.4 mol) of methyl (R)-2-(4-acetylphenoxy) propionate in 356 g of formic acid at 35° C. over the course of 1 h. After stirring at 35° C. for 5 hours, the excess hydrogen peroxide was decomposed with 5 g of sodium sulfite. The mixture was finally concentrated under reduced pressure and subjected to a short-path distillation at 150°–160° C. under 0.5 mbar. Yield: 96% (94–95% enantiomeric excess).

Example 20

Methyl (R)-2-(4-(4-chlorobenzoyloxy)phenoxy) propionate

A mixture of 15.9 g (50 mmol) of methyl (R)-2-(4-(4-chlorobenzoyl)phenoxy)propionate, 25 g (220 mmol) of a 30% strength solution of hydrogen peroxide in water and 200 ml of formic acid was stirred at 35°–40° C. for 13 hours. The mixture was then stirred into a mixture of 0.5 l of methylene chloride and 2 l of water. The organic phase was separated off, dried over sodium sulfate and concentrated under reduced pressure. Yield: 69% (94–95% enantiomeric excess).

Example 21

Methyl (R)-2-(4-hydroxyphenoxy)propionate

A mixture of 45 g (189 mmol) of methyl (R)-2-(4-acetoxyphenoxy)propionate (enantiomeric excess 94–95%), 135 ml of methanol and 2.5 ml of methanol saturated with gaseous hydrogen chloride was refluxed for 5 h and subsequently concentrated. The crude product was purified by distillation at 140° C. under 0.1 mbar. Yield: 96% (94–95% enantiomeric excess).

Example 22

(R)-2-(4-Hydroxyphenoxy)propionic acid

A mixture of 142 g (595 mmol) of methyl (R)-2-(4-acetoxyphenoxy)propionate (enantiomeric excess 94–95%), 560 ml of water and 13 ml of concentrated aqueous hydrochloric acid was refluxed for 3 h, after which 363 g of a mixture of water and acetic acid were removed by distillation under atmospheric pressure. The mixture was then stirred at about 20° C. for 14 h. The solid product was subsequently separated off and dried. Yield: 87.6% (98–99% enantiomeric excess).

We claim:

1. A process for preparing a mixture of (R)- and (S)-2-alkanoylphenoxy)- or (R)- and (S)-2-(4-aroylphenoxy) propionic esters of the general formula I

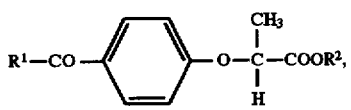

where $R^1$ is aryl, alkyl or aralkyl, and $R^2$ is alkyl, where the mixture contains an enantiomeric excess of at least 90 mol% of (R) or (S) isomer, which comprises reacting a mixture of (R) and (S) enantiomer of a 2-phenoxypropionic ester of the formula II

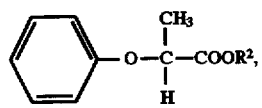

in which the appropriate (R) or (S) isomer is present in said excess, with a carboxylic acid derivative of the formula III

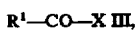

where X is hydroxyl, halogen, $R^1COO$ or a sulffonyloxy radical, in the presence of a Fridel-Crafts catalyst.

2. A process as claimed in claim 1, wherein the reaction is carried out in the presence of a Lewis acid or of a Brönsted acid as Friedel-Crafts catalyst.

3. A process as claimed in claim 1, wherein the reaction is carried out in an inert solvent or diluent.

4. A process as claimed in claim 1, which is applied to the preparation of a mixture in which the (R) enantiomer I is present in excess.

* * * * *

UNITED STATES PATENT AND TRADEMARK OFFICE
CERTIFICATE OF CORRECTION

PATENT NO.: 5,801,272

DATED: September 1, 1998

INVENTOR(S): SIEGEL et al.

It is certified that error appears in the above-identified patent and that said Letters Patent is hereby corrected as shown below:

Col. 8, claim 1, line 38, "sulffonyloxy" should be --sulfonyloxy--.

Col. 8, claim 1, line 39, "Fridel-Crafts" should be --Friedel-Crafts --.

Col. 8, claim 2, lines 2 and 3, "Br" and "önsted" should be together as --Brönsted--.

Signed and Sealed this

Fifteenth Day of December, 1998

Attest:

BRUCE LEHMAN

Attesting Officer

Commissioner of Patents and Trademarks